United States Patent [19]
Farzin-Nia et al.

[11] Patent Number: 6,149,501
[45] Date of Patent: *Nov. 21, 2000

[54] SUPERELASTIC ENDODONTIC INSTRUMENT, METHOD OF MANUFACTURE, AND APPARATUS THEREFOR

[75] Inventors: Farrokh Farzin-Nia, Inglewood; William Otsen, Glendora; Gary Garman, La Verne, all of Calif.

[73] Assignee: Kerr Corporation, Orange, Calif.

[ * ] Notice: This patent is subject to a terminal disclaimer.

[21] Appl. No.: 09/014,139

[22] Filed: Jan. 27, 1998

Related U.S. Application Data

[63] Continuation-in-part of application No. 08/938,507, Sep. 26, 1997, Pat. No. 5,984,679.

[51] Int. Cl.⁷ .......................................................... B24B 1/00
[52] U.S. Cl. .............................................. 451/48; 451/540
[58] Field of Search ................................ 451/28, 48, 102, 451/224, 165, 225, 540; 433/81, 102, 224, 20

[56] References Cited

U.S. PATENT DOCUMENTS

| | | | |
|---|---|---|---|
| 4,443,193 | 4/1984 | Roane | 433/102 |
| 5,044,947 | 9/1991 | Sachdeva et al. | 433/20 |
| 5,106,298 | 4/1992 | Heath et al. | 433/102 |
| 5,302,129 | 4/1994 | Heath et al. | 433/244 |
| 5,429,501 | 7/1995 | Farzin-Nia et al. | 433/21 |
| 5,464,362 | 11/1995 | Heath et al. | 451/48 |
| 5,527,205 | 6/1996 | Heath et al. | 451/48 |
| 5,628,674 | 5/1997 | Heath et al. | 451/48 |
| 5,655,950 | 8/1997 | Heath et al. | 451/48 |
| 5,762,541 | 6/1998 | Heath et al. | 451/48 |
| 5,775,902 | 7/1998 | Matsutani et al. | 433/102 |
| 5,941,760 | 8/1999 | Heath et al. | 451/28 |
| 5,984,679 | 11/1999 | Frazin-Nia et al. | 433/102 |

OTHER PUBLICATIONS

Harmeet Walia et al., An Initial Investigation of the Bending and Torsional Properties of Nitinol Root Canal Files, Journal of Endodontics, vol. 14, No. 7, Jul. 1988.

*Primary Examiner*—Derris H. Banks
*Attorney, Agent, or Firm*—Wood, Herron & Evans, L.L.P.

[57] ABSTRACT

A superelastic endodontic instrument, such as a file, is formed by grinding a superelastic wire to form a file preform or blank, and rotating a first end of the blank while preventing rotation of a second end of the blank. The file blank is maintained in the austenite phase at least until twisted to form a stress induced martensite which is plastically deformed by the twisting. A heat treatment step may be performed prior to twisting, during twisting or after twisting of the preform. The file blank may be heated by electrical heating methods or by submerging the blank in a heated liquid.

112 Claims, 4 Drawing Sheets

SUPERELASTIC ENDODONTIC INSTRUMENT, METHOD OF MANUFACTURE, AND APPARATUS THEREFOR

RELATED APPLICATIONS

This application is a continuation-in-part of U.S. patent application Ser. No. 08/938,507 filed on Sep. 26, 1997, the disclosure of which is hereby fully incorporated by reference herein now U.S. Pat. No. 5,984,679.

FIELD OF THE INVENTION

The present invention generally relates to superelastic endodontic instruments and, more specifically, to instruments such as files or reamers and methods and apparatus for manufacturing such instruments.

BACKGROUND OF THE INVENTION

Over the past several years, endodontic instruments such as root canal files have been manufactured by simultaneously grinding and twisting thin carbon steel or stainless steel rods or wires. Specifically, steel wire blanks are first ground to the desired cross sectional shape, such as square, triangular or rhomboid, and to the appropriate size and taper. The ground blank is then gripped at one end and spring loaded jaws are brought into contact with the ground portion of the blank. As the blank is rotated from the gripped end, the jaws are moved axially away from that end. The jaws therefore twist the rotating blank and form helical flutes into the blank. The longitudinal, ground edges of the blank form helical cutting edges on the file. The axial jaw speed, twisting speed and spring force are controlled to obtain the desired helical configuration.

With the emergence of superelastic materials, such as nickel titanium alloys, endodontic instrument manufacturers are now able to form endodontic root canal files with much more flexibility. This greatly assists the endodontist during use of the file in a root canal procedure. The use of superelastic material, however, causes some significant manufacturing concerns due to the tendency of the material to return to its original shape after the release of an applied force. File blanks manufactured of superelastic materials generally react in this manner to the conventional twisting methods employed for manufacturing carbon and stainless steel files. Moreover, if superelastic file blanks are over-stressed, such as by being twisted too much during the fluting procedure, the material is subject to failure. For reasons such as these, current manufacturers of endodontic files may resort to grinding the helical profile directly into the superelastic blanks while applying no twisting forces to the blanks. These direct grinding methods are time consuming and expensive. They also limit the variety of cross sectional shapes that may be formed in the final product.

With the above background in mind, it would be desirable to provide a method of manufacturing a wide variety of superelastic endodontic appliances, such as files, using twisting and grinding techniques. In short, it would be advantageous to retain the benefits of superelastic materials and the benefits of a twisting and grinding procedure that simplifies manufacture and allows the production of a wide variety of file cross sections.

SUMMARY OF THE INVENTION

The present invention provides a superelastic endodontic instrument, which is preferably a file or reamer, having increased torsional and bending flexibility, as compared to conventional steel files, and manufactured by improved processes relative to prior superelastic file production techniques. Generally, the invention provides a process in which a superelastic endodontic instrument preform or blank may be ground and then twisted with plastic deformation, that is, maintenance of the twisted shape, without over-stressing the material into failure.

The unique process of this invention involves maintaining the instrument blank in the austenite phase of the superelastic material at least prior to twisting and, preferably, prior to and during the twisting operation. To maintain the blank in the austenite phase, the blank is preferably maintained above the austenite finish temperature (Af) of the particular superelastic material. The blank is more preferably maintained in the working temperature range Tw of the superelastic material. For a wide variety of superelastic alloys, this range would be between 200° F.–400° F. The material of the blank is converted from the austenite phase to the martensite phase by the stress applied during the twisting operation. The material undergoing stress induced martensite transformation is plastically deformed during twisting so that the fluted profile is retained after completion of the twisting process. Due to the ability to pregrind a file blank, for example, it is possible to fabricate a superelastic endodontic file having many different transverse cross sectional shapes, such as those conventionally obtained with steel materials.

In another aspect of this invention, the elevation in temperature to the austenite finish temperature Af of the superelastic blank may be accomplished through several different methods, such as ambient, induction, joulian, or radiant heating, or submersion within a heated liquid. Ambient heating, for example, may be accomplished in an oven while induction heating may utilize an inductive heating coil surrounding the blank during the twisting operation.

Submersion within a heated liquid can allow the blank to be heated in a rapid and controlled manner. The heated liquid may be oil or a salt solution, or other liquids that do not boil below or close to the Af of the particular superelastic metal. Fluting apparatus is provided generally above a vessel containing the liquid and includes a rotary motion mechanism for holding and rotating an instrument blank, such as a file blank, a clamping mechanism that receives a ground portion of the file blank and a linear or axial motion mechanism for moving the clamping mechanism along the longitudinal axis of the file blank at a rate which is proportional to the rate of rotation. According to this heating alternative, the twisting operation is preferably performed with the ground portion of the blank submerged in the heated liquid. After the twisting process is complete, the fluted, superelastic file may then undergo subsequent quenching or heat treatment operations in order to achieve the desired physical properties.

Additional objects and advantages of the invention will become more readily apparent to those of ordinary skill in the art upon review of the following detailed description of the preferred embodiment taken in conjunction with the drawings.

DETAILED DESCRIPTION OF THE PREFERRED EMBODIMENTS

Superelastic materials are typically metal alloys which return to their original shape after substantial deformation. Superelastic alloys such as nickel titanium (NiTi) can withstand several times more strain than conventional materials, such as stainless steel, without becoming plastically deformed. Further, a superelastic material will generally recover approximately 6% after twisting at ambient temperature while a stainless steel will recover only 1–2% after twisting. Typically, superelastic alloys undergo a stress induced martensitic transformation which allows for shape memory properties. Shape memory and superelasticity are found in stoichiometric NiTi, near-equiatomic Ni-Ti, for example, 50.8 atomic percent Ti and 49.2 atomic percent Ni, Ni-Ti-Cu, Ni-Ti-Nb and Ni-Ti-Fe alloys as well as beta-phase titanium or other Ti based alloys. Examples of suitable nickel-titanium alloys in various stoichiometric ratios are disclosed in U.S. Pat. No. 5,044,947 (nickel-titanium-copper alloy) and U.S. patent application Ser. Nos. 08/221,638 and 08/454,016, inventor Sachdeva et al., entitled "NiTiNb Alloy Processing Method and Articles Formed Thereby" (nickel-titanium-niobium-alloy). The disclosures of U.S. Pat. No. 5,044,947 and the aforesaid applications are hereby incorporated by reference.

The specific alloy composition used for the endodontic instrument of this invention is not critical as the invention may utilize many materials which exhibit superelastic characteristics. U.S. Pat. No. 5,429,501, which is hereby incorporated in its entirety by reference herein, discloses superelastic and shape memory beta-phase titanium. To form beta-phase titanium, metallic titanium may be alloyed with molybdenum, chromium, zirconium, tin, vanadium, iron or niobium. Other compositions such as Cu-Zn alloys are also known to be superelastic and are suitable for use in the present invention. Another material suitable for use in the present invention is a work hardened nickel titanium having a martensitic crystal structure, such as that sold under the tradename NITANOL for orthodontic wires by Unitek Corp., Arcadia Calif.

Figure 6:
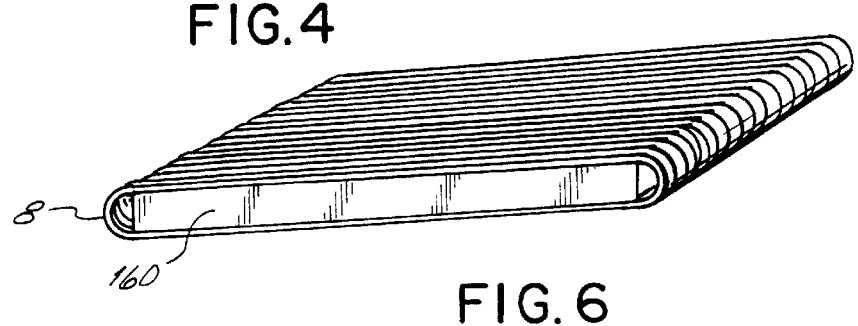
FIG. 6 is a perspective view of the apparatus used in straightening superelastic wire.

Superelastic materials have a temperature range in which the material may be permanently deformed. This range is known as the working temperature range Tw. When a superelastic wire is heated to a temperature in the working temperature range Tw, the wire may be permanently deformed so that when the wire is cooled, the deformed shape is maintained. Typically, the superelastic wire is packaged in coils and should be straightened prior to grinding and twisting. One method of straightening the wire 8 is to wrap the wire around a mandrel 160 as shown in FIG. 6. The mandrel 160 is then placed in a furnace and the wire 8 is heated into the Tw. The wire 8 is then cooled, removed from the mandrel and the curved ends are trimmed.

Superelastic alloys are in the martensitic phase when they are below the austenitic transformation temperature Af, i.e., the temperature at which the material is about 100% austenite. These alloys retain their deformed shape when subjected to stress in the martensitic phase. However, the shape memory property returns the deformed material to its original predeformation configuration when heated above Af. In the present invention it is preferred to use an alloy having an Af temperature lower than about 37° C. (i.e., body temperature) so that the instrument will be in the austenitic phase during use in the human body.

When the superelastic material is twisted, the material may form a stress induced martensite phase since less energy is necessary to stress induce and deform martensite than to deform austenite. If the file preform is deformed at room temperature and there is not enough strain to induce plastic deformation of the martensite phase, the wire will spring back to its original shape once the twisting force is released. It is also possible to permanently deform superelastic material by heating within the Tw range prior to and during twisting. A typical superelastic material will have a Tw range of 200° F.–400° F. Another method of permanently deforming a preform or blank according to the invention is by performing a rapid twist step to heat the superelastic material by internal friction to a temperature at which the material forms a stress induced martensite.

As used herein, the terms shape-memory alloy and superelastic material or alloy or similar terms are intended to include all suitable alloy compositions which possess shape-memory and/or superelastic properties, respectively. Moreover, the term superelastic is intended to mean the ability of a material to withstand at least twice as much strain as stainless steel materials can withstand without plastic deformation. The term shape memory is intended to mean the ability of a wire to recover to its original state by the use of temperature. The term rhombus or rhomboidal is intended to define a geometric shape, having four major sides, which is substantially a parallelogram, i.e., including four equal sides and no internal right angles.

Figure 1:
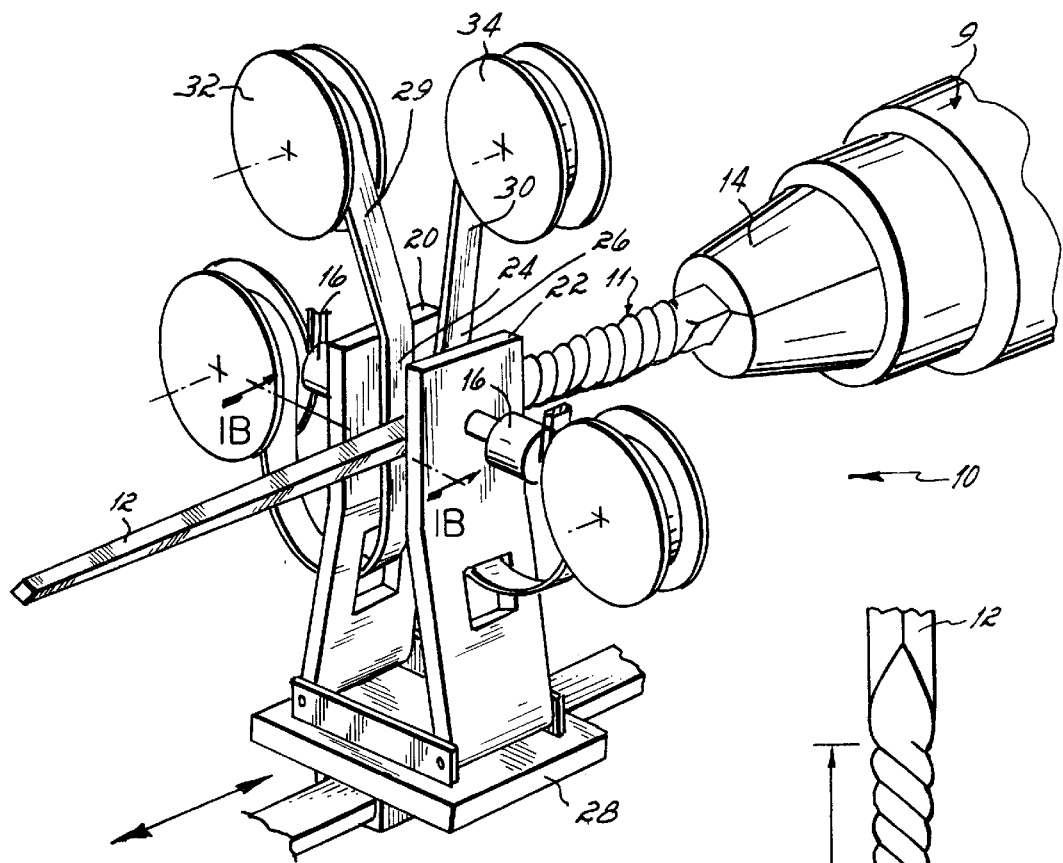
FIG. 1 is a schematic perspective view of one type of apparatus used in fabricating a superelastic file in accordance with the present invention.
Figure 1B:
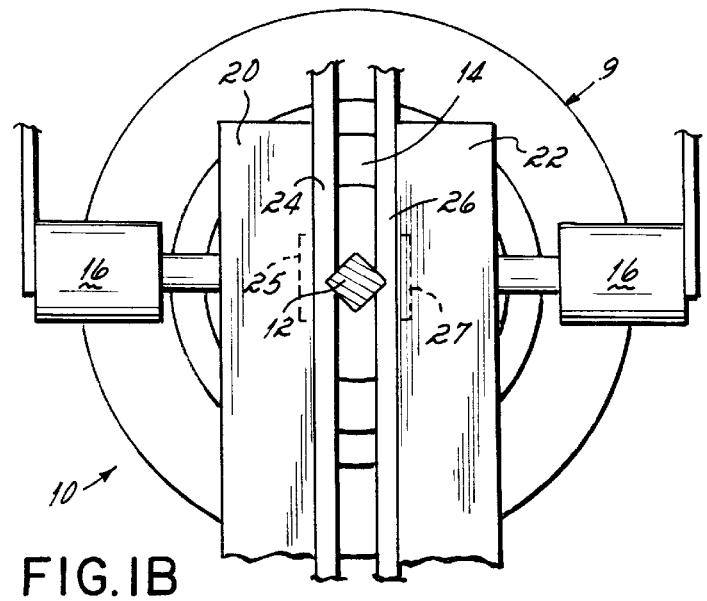
FIG. 1B is an enlarged cross-sectional view taken on line 1B—1B of FIG. 1A.

The files and file-forming processes of this invention are implemented, in one preferred embodiment, with an apparatus such as apparatus 10 depicted in FIG. 1. Prior to twisting, file preforms or blanks are ground to the desired shape, including length, transverse cross-section and taper, on any one of the devices shown in FIGS. 2, 3, or 5.

Figure 1A:
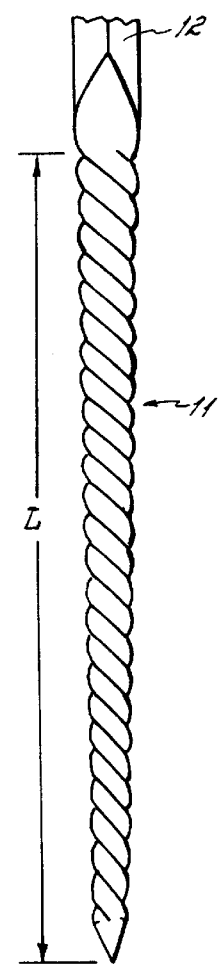
FIG. 1A is a side view of a file formed on the apparatus of FIG. 1.
Figure 2:
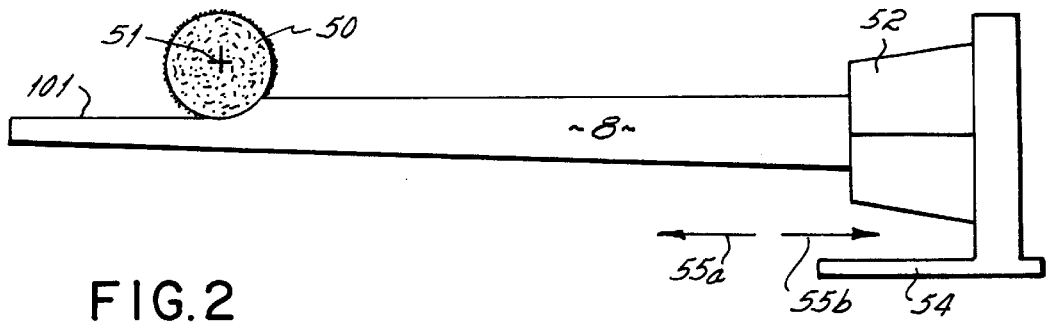
FIG. 2 is a schematic side view of one apparatus for forming a flat surface along the length of a file blank.

Referring to FIG. 2, cylindrical superelastic rods or wires 8 are ground to form file preforms or blanks 12 which are subsequently twisted to form helically fluted files 11. Cylindrical rod or wire 8 is mounted into collet 52 which is fixedly mounted upon a stage 54 which is selectively horizontally movable in opposite directions as designated by arrows 55a and 55b. Once rod 8 is mounted in the collet 52, grinding wheel 50 is lowered into contact with the rod 8. Stage 54 is then advanced horizontally rightwardly, as is seen in FIG. 2, to move collet 52 and rod 8 axially so that a flat surface 101 is ground on one side of the rod 8. After one such flat, that is, flat surface, has been ground along the working length L (see FIG. 1A) of the rod, grinding wheel 50 is lifted vertically, and stage 54 is moved axially leftwardly to the initial or home position so that the grinding wheel 50 is aligned with the upper portion of the inner end of the working length of the partially ground rod. Collet 52 is then indexed about its central axis by a predetermined angle, the magnitude of which depends on the number of flutes desired in the finished file. Indexing rotational angles of 180°, 120° and 90° are employed for 2, 3 and 4 flute files, respectively. It is also possible to rotate the collet by a series of angles (e.g. 60°, 120°, 60°) to obtain a file preform having a rhomboidal cross section. Grinding wheel 50 is then lowered to the desired depth of contact with the rod 8, and stage 54 is then moved rightwardly to move rod 8 axially past grinding wheel 50 to grind the second flat surface on the file blank. The foregoing process is repeated until all the flats have been ground on the file blank.

Figure 2A:
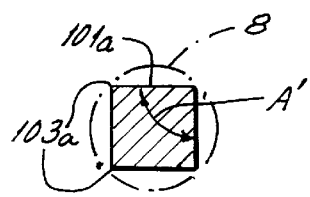
FIGS. 2A, 2B, 2C and 2D are transverse cross-sectional views, perpendicular to the longitudinal axis of the finished file or the file blank using the apparatus of FIG. 2 or FIG. 6.
Figure 2B:
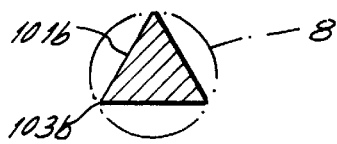
Figure 2C:
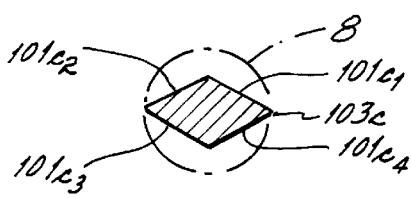

As noted, by varying the angle which collet 52 indexes rod 8, it is possible to form file blanks having three or more apices 103 shown generally in FIGS. 2A–2C. The apices 103 of the preground file blank, once twisted, and permanently helically fluted, form the cutting edges of the helically fluted file. Typically, endodontic files include three or four apices or helical cutting edges 103.

Figure 2D:
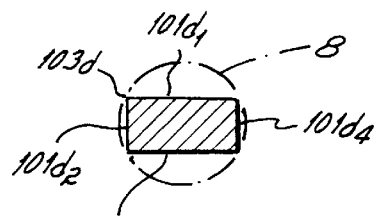

In order to form a file blank having a square transverse cross section as shown in FIG. 2A, rod 8 is indexed 90° after each flat surface 101 is ground. In order to form a file blank having three apices and a triangular transverse cross section, the rod is indexed 120° after each flat surface is formed (as shown in FIG. 2B). Using the method of the present invention it is also possible to form a file having a rhomboidal transverse cross section (FIG. 2C). This is accomplished by grinding a first flat surface $101c_1$; indexing the rod 60° clockwise as viewed in FIG. 2C and grinding a second flat surface $101c_2$; indexing the rod 120° clockwise as viewed in FIG. 2C and grinding a third flat surface $101c_3$; and indexing the rod 60° clockwise as viewed in FIG. 2C and grinding the fourth flat surface $101c_4$. It is not necessary to change the initial depth of cut of the wheel to fabricate the square, triangular and rhomboidal preforms shown in FIGS. 2A–2C, respectively. However, in order to fabricate a preform having a rectangular cross-section, as shown in FIG. 2D, the initial depth of cut may be adjusted prior to forming each flat side or may be adjusted after opposing pairs of edges are ground. For example, as seen in FIG. 2D, a first flat side $101d_1$, is ground; the rod 8 is then indexed 90°, the initial depth of cut reduced and a second flat side $101d_2$ is ground; rod 8 is then indexed 90°, the initial depth of cut is increased to the depth used for the cut of side $101d_1$ and a third flat side $101d_3$ is ground; rod 8 is then indexed 90°, the initial depth of cut is reduced to the depth used for the cut of side $101d_2$ and fourth side $101d_4$ is ground. It is also possible to grind flat side $101d_1$, index the rod 180°, and grind flat side $101d_4$; index the rod 90° and decrease the initial depth of cut and grind flat side $101d_2$; and finally index the rod 180° and grinding the final flat side $101d_3$.

Figure 3:
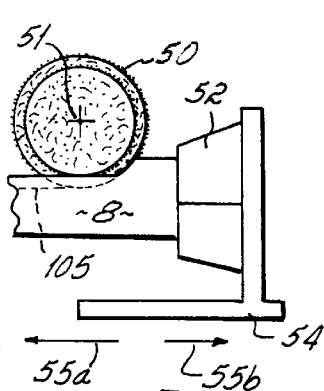
FIG. 3 is a schematic side view of an apparatus similar to FIG. 2 for forming a concave surface along the length of a file blank.
Figure 3A:
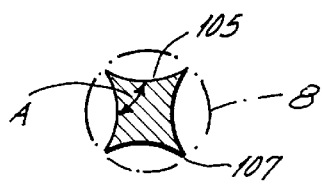
FIGS. 3A, 3B and 3C are transverse cross-sectional views, perpendicular to the longitudinal axis of the finished file or the file blank, showing concave surfaces formed on file blanks, using the apparatus of FIG. 3.
Figure 3B:
Figure 3C:
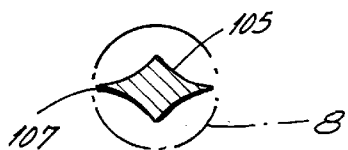

It is possible to form a variety of different cross sectional shapes by varying the surface of the grinding wheel and/or the index angles. For example, by dressing the surface of grinding wheel 50 so that the surface is convexed, as shown in FIG. 3, it is possible to form ground surfaces 105 having the concave shapes shown in FIGS. 3A, 3B and 3C, rather than the flat shapes of the surfaces 101 shown in FIGS. 2A, 2B and 2C. When the surface of the grinding wheel 50 is convexed, the angle A of the apices 107 (FIG. 3A) is more acute for a file having the same index angle and number of sides than is angle A' of the apices 103 (FIG. 2A) when the surface of the grinding wheel 50 is flat (FIG. 2). While angle A is more acute and provides a sharper cutting edge, that edge is weaker due to the lower amount of material at the apex. Thus, the apices shown in FIGS. 2A–2C are more rugged to maintain a usable edge and provide for a longer working life.

Figure 5:
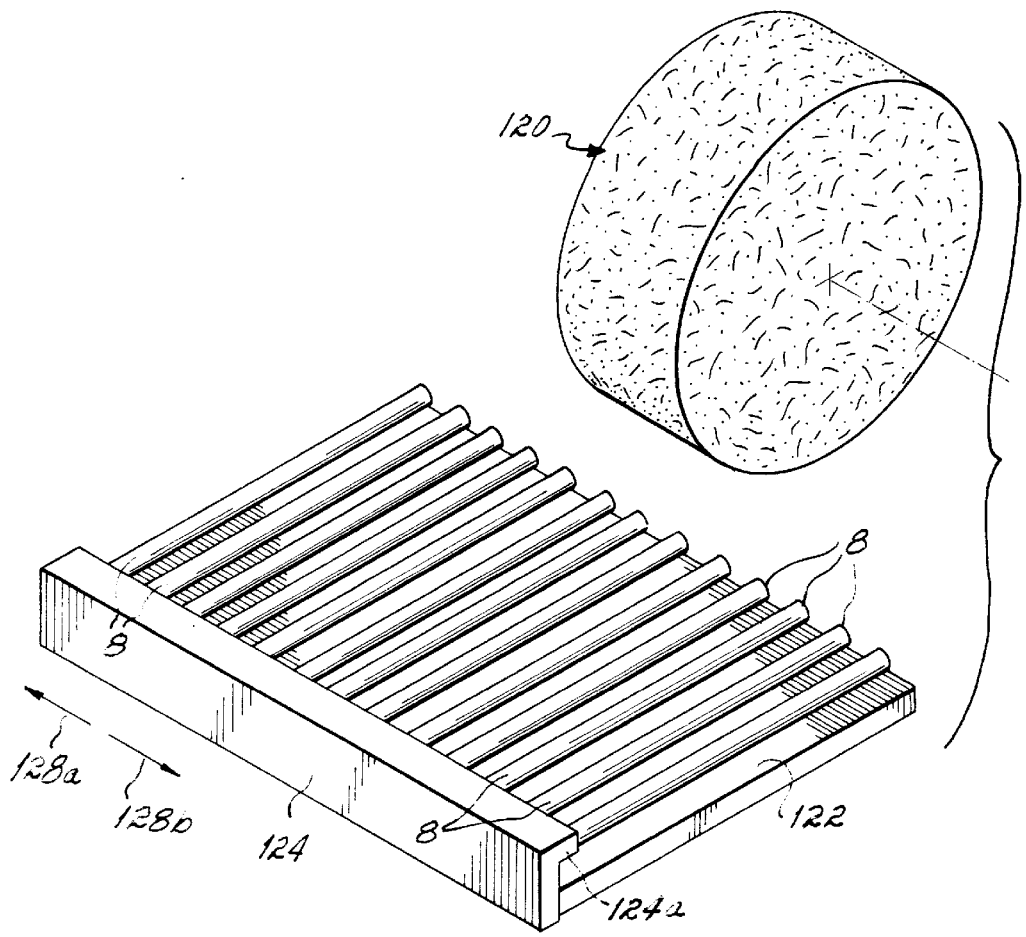
FIG. 5 is a perspective view of another apparatus for forming flat surfaces along the length of a number of file blanks.
Figure 4:
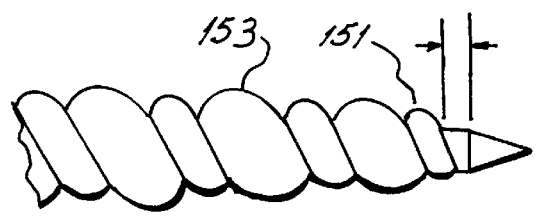
FIG. 4 is a detail view of a rhomboidal file tip.

Another device for grinding cylindrical rods 8 is shown in FIG. 5. FIG. 5 shows a wide grinding wheel 120 which moves transversely to the longitudinal axes of a large number of rods 8 to grind a flat surface onto the rods. The cylindrical rods 8 are placed upon rest 122. The rods 8 are disposed in parallel and extend along substantially the entire width of the rest 122. The parallel rods 8 are held by retainer 124 which is movable along the length of rest 122 as shown by opposing arrows 128a and 128b. Movable retainer 124 includes lateral projection 124a which extends over an end portion of rods 8 to secure the rods to rest 122 and prevent the rotation of the rods during grinding. Once rods 8 are retained between the lateral projection 124a and the rest 122, grinding wheel 120 moves back and forth across the width of rest 122 to grind a flat surface on the entire working length of each rod 8. Typically, the grinding 120 wheel moves across each rod twice, once while traveling away from projection 124a and once while traveling toward projection 124a. During grinding, the wheel 120 may be moved straight across the rods or may move in a figure eight or zigzag pattern. The grinding wheel is preferably a porous wheel such as an ANSI standard C-601V wheel rotating at rate between 3,000 and 8,000 surface feet per minute and preferably about 5,000 surface feet per minute. The material is passed under the wheel at a feed rate between about 50 and 100 lineal feet per minute, and preferably about 75 lineal feet per minute.

After grinding a first flat side, the movable retainers 124 is translated with respect to the rest 122. The lateral projection 124a of the retainers 124 remains in contact with rods 8 so that the movement of the retainer along the direction shown by arrows 128a, 128b causes each rod to rotate by a predetermined angle about the longitudinal axis of the rods 8. Once the rotation is complete, a second flat surface is ground across the working length of the rod. Depending upon the desired cross section of the file 11, the rods 8 are typically rotated and ground one or more times.

After the superelastic file blanks have been ground to the desired cross-sectional file preform shape they are preferably heated to a temperature above ambient temperature prior to, during and subsequent to the twisting operation using thermal or frictional energy or a combination thereof. This temperature is preferably above the austenite finish temperature Af of the particular superelastic material and can be as high as the working temperature range Tw of the material.

The heating process may externally heat the wire preform in the collet 14 by the provision of induction coils, radiant heating elements or electrodes to provide for joulian heating. The temperature to which the preform is heated is based upon the specific alloy used. A temperature range of 200° F.–400° F. is contemplated to be typical. Alternatively, the files can be heated without the application of heat from an external heat source by twisting rapidly so that internal friction heats the file.

Once the file preforms are formed, they are twisted or heated and twisted on a device such as that shown in FIG. 1. The twisting apparatus 10, shown in FIG. 1, includes a drive head 9 which rotates about a horizontal axis. Extending from the drive head 9 is a collet 14 which circumferentially grips and secures the proximal or inner end of a preformed ground file blank 12 for rotation about the longitudinal axis thereof. The distal or outer end portion of the file blank 12 is secured by opposing jaws 20, 22, which are mounted on a stage 28 which moves parallel to the longitudinal axis of the file blank (horizontally as shown in FIG. 1), away from collet 14 at a predetermined rate as the collet rotates to twist the file blank 12. At least one of the jaws includes a spring or air cylinder 16 so that it may be compressed against the opposing jaw with a constant force. Each jaw includes a protectant layer 24, 26 which is malleable and able to withstand the working temperature of the file blank 12. Brass is one material known to be suitable. With each subsequent file formed, the jaws 20, 22 are provided with a new protectant layer 24, 26 from strips 29, 30 from a source 32, 34 such as take-off reels. The protectant layer may optionally be contacted by a heating element 25, 27 which may heat by any suitable process, such as an electrical heating process of joulian, radiant or induction heating or may be supplied with a heated fluid such as steam or oil.

In order to optimize the superelastic properties of the finished file it is desirable, although not essential, to heat treat the twisted files. The heat treatment may be performed in any furnace with air circulation. The radiant heating elements or electrodes to provide for joulian heating can be used for the post twist heat treatment.

Typically the files are made in a variety of working lengths varying from 19–30 mm. The specific variables which are typically controlled in fabricating such files are set forth in the Tables 1 and 2. In Tables 1 and 2 the variables A and B represent the minimum thickness of the transverse cross section at 16.00 mm and 3.00 mm, respectively, from the tip. The variables C and D represent the maximum thickness of the transverse cross section at 16.00 mm and 3.00 mm, respectively, from the tip.

Table 1 describes the characteristics of a twisted rhomboidal file. In observing the longitudinal cross section of a rhomboidal file there are alternating large flutes 153, resulting from the major axis of the rhombus, and small flutes 151, resulting from the minor axis of the rhombus. In Table 1 the column entitled Tight Flute Limit includes two values. The first value is the minimum acceptable length of a small flute 151 resulting from the twisting of the minor axis of the rhombus. The second value is the minimum acceptable length of a large flute 153 resulting from the twisting of the major axis of the rhombus. Similarly, the column entitled Loose Flute Limit includes two values. The first value is the maximum acceptable length of a small flute 151 resulting from the twisting of the minor axis of the rhombus. The second value is the maximum acceptable length of a large flute 153 resulting from the twisting of the major axis of the rhombus. In Table 1 the column labeled T max represents the maximum acceptable length of the untwisted portion at the distal tip of the file. In Table 2 the value L is the length of the ground portion of the rod.

Figure 7:
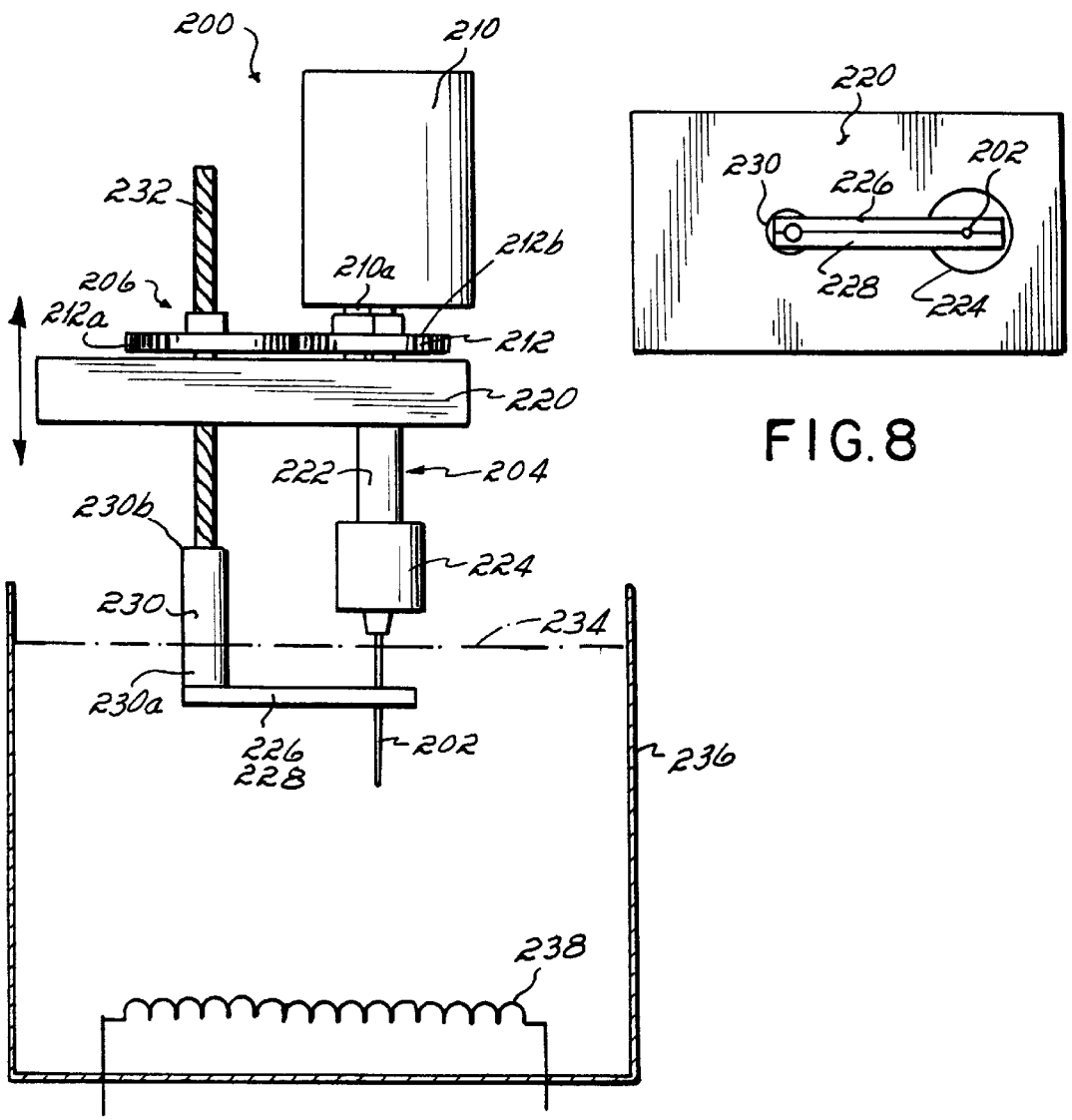
FIG. 7 is a schematic elevational view of another type of apparatus used in fabricating a superelastic file of the present invention in conjunction with a heated liquid.

Referring now to FIG. 7, an apparatus 200 is shown for forming a superelastic endodontic file blank 202 into a fluted, superelastic file. File blank 202 has been ground, such as in accordance with the above descriptions, before being fluted by apparatus 200. Apparatus 200 generally comprises a rotary motion mechanism 204 operatively connected to a linear or axial motion mechanism 206 similar to apparatus 10 of FIG. 1. Each mechanism 204, 206 is connected to file blank 202 for purposes to be described. Rotary motion mechanism 204 and linear motion mechanism 206 may be conventional mechanisms known in the art for forming helical flutes on endodontic files. Each mechanism 204, 206 is operated by a suitable electric motor 210. A gear drive 212 is connected in a conventional manner between an output 210*a* of motor 210 and linear motion mechanism 206 to convert the rotary motion of motor 210 into linear motion. Gear drive 212 is shown to simply include two gears 212*a*, 212*b*, for simplicity, but it will be understood that idler gears may be used between gears 212*a*, 212*b*. Such idler gears are conventionally used to set the material feed rate. A support plate 220 is provided generally for connecting rotary motion mechanism 204 to linear motion mechanism 206. Support plate 220 can also serve as a mounting plate for a mechanism (not shown) used to raise and lower apparatus 200, for reasons to be described.

Figure 8:
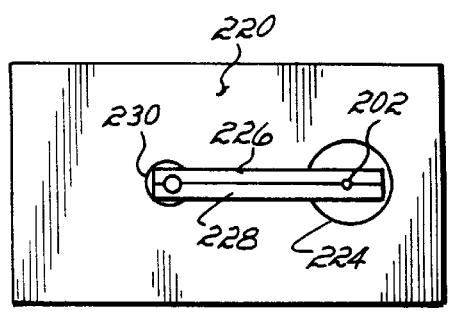
FIG. 8 is a bottom view of the apparatus shown in FIG. 7.

Rotary motion mechanism 204 further comprises a rotary shaft 222 which may be directly coupled to output shaft 210*a* of motor 210. A conventional collet 224 is provided for holding a proximal end of superelastic file blank 202. Superelastic file blank 202 further has its ground portion or working length held between a pair of spring-loaded clamping jaws 226, 228, as best shown in FIG. 8. Clamping jaws 226, 228 are held at a relative lower end 230*a* of a clamping jaw support 230. Clamping jaw support 230 preferably has a conventional biasing mechanism to force jaws 226, 228 toward one another with a desired clamping force. Further, clamping jaw support 230 holds a helical threaded shaft 232 for rotation at a relative upper end 230*b*. Helical threaded shaft 232 is also held within internal threads of gear member 212*a* of gear drive 212 such that, upon operation of gear drive 212 by motor 210, gear member 212*a* will rotate and also rotate helical threaded shaft 232. This will move shaft 232 linearly along its longitudinal axis thereby moving jaw support 230 and jaws 226, 228 along the length of the pre-ground superelastic file blank 202.

In accordance with one aspect of the invention, a heated liquid 234 contained in a vessel 236 receives the ground portion of file blank 202 during a twisting and fluting operation. The heated liquid media 234 may, for example, comprise a salt solution or other suitable liquids such as oil. Preferably, the chosen liquid will have a boiling temperature preferably above the Af temperature or even above the Tw of the particular superelastic material. Presently, it is contemplated that a suitable operating temperature for liquid 234 is approximately 500° C. or above. Again, it is preferable that the liquid does boil at the chosen operating temperature. Liquid 234 may be heated by any conventional manner, such as with an electrical heating element 238 or a heating jacket.

For purposes of describing the operation of the apparatus 200 shown in FIGS. 7 and 8, one contemplated example involves placing a ground file blank 202, formed of a superelastic metallic alloy and formed with a rhomboid cross section as generally described above, within collet 224. Clamping jaws 226, 228 may then be placed about a proximal, ground end of file blank 202 adjacent collet 224. Apparatus 200 may then be lowered toward a heated liquid comprised of a salt solution heated to a temperature of about 500° C. Blank 202 should be lowered until the ground portion is submerged within heated liquid 234. After about five seconds, a fluting operation may be carried out by moving linear or axial motion mechanism 206 downwardly at a speed of about 6 inches/min. Rotation of blank 202 may be carried out by mechanism 204 at a corresponding rate which forms a desired number of twists. When the fluting jaws 226, 228 reach the relative lower tip end of ground file blank 202, the fluting operation is complete and apparatus 200 may be lifted from heated liquid 234 and removed from collet 224. Quenching or heat treating of the finished file may then be carried out if appropriate.

It will be appreciated that different alloy compositions will possess a different shape-memory characteristic, a different transformation temperature (Af), a different modulus of elasticity, and a different working temperature range Tw. It is within the skill of one in the art based upon the teachings of the present invention to adjust the heating, twisting and heat treating steps based upon the specific properties of the material used.

While the present invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details, representative apparatus and method as shown and described. This has been a description of the present invention, along with the preferred methods of practicing the present invention as currently known. However, the invention itself should only be defined by the appended claims, wherein we claim:

TABLE 1

| Size | Wire Dia. (Inches) | No. of Twists | No. of Edges ± 1 | Tight Flute Limit (mm) | Loose Flute Limit (mm) | A (mm) | B (mm) | T Max. (mm) |
| --- | --- | --- | --- | --- | --- | --- | --- | --- |
| 40  | .035 | 7    | 28 | 0.368/0.500 | 0.673/0.813 | 0.720 | 0.460 | 0.25 |
| 45  | .035 | 6.5  | 26 | 0.406/0.622 | 0.711/0.927 | 0.770 | 0.510 | 0.34 |
| 50  | .037 | 6.25 | 25 | 0.394/0.660 | 0.699/0.965 | 0.820 | 0.560 | 0.38 |
| 55  | .041 | 6    | 24 | 0.381/0.660 | 0.686/0.965 | 0.870 | 0.610 | 0.38 |
| 60  | .041 | 5.75 | 23 | 0.406/0.787 | 0.711/1.092 | 0.920 | 0.660 | 0.38 |
| 70  | .048 | 5.5  | 22 | 0.279/0.838 | 0.813/1.372 | 1.020 | 0.760 | 0.38 |
| 80  | .051 | 5.25 | 21 | 0.292/0.851 | 0.826/1.384 | 1.120 | 0.860 | 0.38 |
| 90  | .055 | 4.75 | 19 | 0.292/0.851 | 0.927/1.473 | 1.220 | 0.960 | 0.38 |
| 100 | .063 | 4    | 16 | 0.318/1.016 | 0.927/1.626 | 1.320 | 1.060 | 0.38 |
| 110 | .063 | 3.75 | 15 | 0.381/1.088 | 1.092/1.788 | 1.420 | 1.160 | 0.38 |
| 120 | .069 | 3.5  | 14 | 0.434/1.194 | 1.146/1.905 | 1.520 | 1.260 | 0.38 |
| 130 | .076 | 3.25 | 13 | 0.470/1.222 | 1.181/1.933 | 1.620 | 1.360 | 0.38 |
| 140 | .076 | 3    | 12 | 0.518/1.283 | 1.232/1.994 | 1.720 | 1.460 | 0.38 |

TABLE 2

| Size | Sides | Rod Diameter (mm) | A (mm) | B (mm) | L (mm) | C (mm) | D (mm) |
| --- | --- | --- | --- | --- | --- | --- | --- |
| 08  | 4 | 0.51 | 0.305–0.279 | 0.122–0.096 | 20.98–19.81 |             |             |
| 10  | 4 | 0.51 | 0.323–0.297 | 0.132–0.107 | 20.98–19.81 |             |             |
| 15  | 4 | 0.56 | 0.356–0.330 | 0.170–0.145 | 20.98–19.81 |             |             |
| 20  | 4 | 0.61 | 0.394–0.368 | 0.208–0.183 | 20.98–19.81 | .290–.278   | .551–.526   |
| 25  | 4 | 0.66 | 0.437–0.411 | 0.244–0.218 | 20.98–19.81 | .340–.315   | .612–.587   |
| 30  | 4 | 0.71 | 0.470–0.455 | 0.279–0.254 | 20.98–19.81 | .389–.363   | .660–.635   |
| 35  | 4 | 0.79 | 0.503–0.478 | 0.312–0.287 | 21.34–20.32 | .437–.411   | .706–.681   |
| 40  | 4 | 0.79 | 0.533–0.508 | 0.356–0.330 | 21.34–20.32 | .498–.427   | .765–.739   |
| 45  | 4 | 0.89 | 0.577–0.551 | 0.386–0.361 | 21.59–20.32 | .541–.516   | .810–.785   |
| 50  | 4 | 0.94 | 0.622–0.597 | 0.422–0.396 | 21.59–20.32 | .589–.564   | .874–.848   |
| 55  | 4 | 0.94 | 0.655–0.630 | 0.462–0.437 | 21.59–20.32 | .648–.622   | .922–.897   |
| 60  | 4 | 1.04 | 0.701–0.676 | 0.495–0.470 | 22.35–20.95 | .696–.671   | .986–.960   |
| 70  | 4 | 1.12 | 0.767–0.727 | 0.574–0.528 | 22.35–20.98 | .800–.760   | 1.077–1.036 |
| 80  | 4 | 1.22 | 0.858–0.818 | 0.655–0.610 | 22.35–20.98 | .922–.881   | 1.207–1.166 |
| 90  | 4 | 1.40 | 0.945–0.895 | 0.731–0.691 | 23.01–20.98 | 1.019–.978  | 1.314–1.273 |
| 100 | 4 | 1.60 | 0.993–0.953 | 0.795–0.755 | 24.38–23.01 | 1.109–1.069 | 1.395–1.354 |
| 110 | 4 | 1.60 | 1.151–1.111 | 0.940–0.900 | 24.89–23.62 | 1.311–1.270 | 1.617–1.577 |
| 120 | 4 | 1.75 | 1.214–1.174 | 0.998–0.958 | 24.89–23.62 | 1.393–1.351 | 1.706–1.666 |
| 130 | 4 | 1.93 | 1.299–1.258 | 1.082–1.042 | 24.89–23.62 | 1.510–1.469 | 1.824–1.783 |
| 140 | 4 | 1.93 | 1.384–1.344 | 1.151–1.111 | 24.89–23.62 | 1.606–1.565 | 1.945–1.905 |

What is claimed is:

1. An endodontic instrument formed by plastic deformation of a blank having a longitudinal axis and formed from a superelastic material, wherein the instrument is formed by the steps of:

transforming the superelastic material of the blank into an austenite phase; and twisting the blank about the longitudinal axis to form an instrument having helically shaped edges.

2. The endodontic instrument of claim 1 wherein the superelastic metal of the blank transforms to martensitic phase during the twisting step.

3. The endodontic instrument of claim 1 wherein the superelastic material is a Ti alloy.

4. The endodontic instrument of claim 3 wherein said superelastic material is selected from the group consisting of stoichiometric NiTi, near-equiatomic Ni-Ti, Ni-Ti-Nb alloys, Ni-Ti-Fe alloys, Ni-Ti-Cu alloys, beta-phase titanium alloys and combinations thereof.

5. The endodontic instrument of claim 3 wherein said superelastic material is at least about 40 atomic percent Ti.

6. The endodontic instrument of claim 1 wherein said instrument is selected from the group consisting of files and reamers.

7. The endodontic instrument of claim 1 wherein the transforming step includes external heating of the blank.

8. The endodontic instrument of claim 1 further comprising heating the blank by internal friction during twisting to maintain the blank in the austenite phase.

9. The endodontic instrument of claim 1 wherein the blank is transformed to the austenite phase by heating the blank in a bath of heated liquid.

10. The endodontic instrument of claim 9 wherein the blank remains submerged in the bath during twisting.

11. An superelastic endodontic instrument formed by plastic deformation of a blank having a longitudinal axis and formed from a superelastic material, wherein the instrument is formed by the steps of:

heating the blank to transform the superelastic material to an austenite phase; and twisting the blank about the longitudinal axis to form an instrument having helically shaped edges.

12. The endodontic instrument of claim 11 wherein the superelastic material transforms to martensitic phase following the twisting step.

13. The endodontic instrument of claim 11 wherein the superelastic material is a Ti alloy.

14. The endodontic instrument of claim 13 wherein said superelastic material is selected from the group consisting of stoichiometric NiTi, near-equiatomic Ni-Ti, Ni-Ti-Nb alloys, Ni-Ti-Fe alloys, Ni-Ti-Cu alloys, beta-phase titanium alloys and combinations thereof.

15. The endodontic instrument of claim 13 wherein said superelastic material is at least about 40 atomic percent Ti.

16. The endodontic instrument of claim 11 wherein said instrument is selected from the group consisting of files and reamers.

17. The endodontic instrument of claim 11 wherein the heating step includes external heating of the blank.

18. The endodontic instrument of claim 11 wherein the heating step includes heating of the blank by internal friction during twisting.

19. The endodontic instrument of claim 11 wherein the heating step is performed in a bath of heated liquid.

20. The endodontic instrument of claim 19 wherein the bath is comprised of a salt solution.

21. The endodontic instrument of claim 19 wherein the bath is comprised of oil.

22. A method of forming an endodontic file from a performed wire blank comprising a superelastic material and having a longitudinal axis and a predetermined transverse cross-sectional shape with apices for defining longitudinal edges along a working length of the file, the method comprising the steps of:

twisting the blank about its longitudinal axis to permanently, helically deform said blank and convert said longitudinal edges into helically shaped cutting edges; and maintaining the blank in an austenite phase at least until immediately prior to the twisting step.

23. The method of claim 22 wherein the superelastic material transforms to martensite phase during the twisting step.

24. The method of claim 23 wherein the martensite phase is a stress induced martensite phase.

25. The method of claim 24 wherein the stress induced martensite phase includes plastic deformation of the blank during the twisting step.

26. The method of claim 22 wherein, prior to the twisting step, the method further comprises the step of grinding at least one elongated narrow surface along the exterior of the blank for a distance approximately equal to the working length of the file.

27. The method of claim 26 wherein the predetermined cross-section of the blank along the working length has a cross section selected from the group consisting of three-sided and four-sided polygons.

28. The method of claim 27 wherein the predetermined cross-sectional shape is substantially rhomboidal.

29. The method of claim 26 further comprising the step of heating the file blank to a temperature above the austenite finish temperature Af of the superelastic material prior to twisting.

30. The method of claim 26 further comprising the step of heating the blank to a temperature of about 200°–400° F. prior to twisting.

31. The method of claim 29 wherein the heating step is performed by an electrical heating process selected from the group consisting of radiant, joulian and induction heating.

32. The method of claim 29 wherein the heating step is performed in a bath of heated liquid.

33. The method of claim 32 wherein the bath is comprised of salt solution.

34. The method of claim 26 further comprising the step of heat treating the blank by heating to a temperature within the Tw range of the superelastic material subsequent to the twisting step.

35. The method of claim 34 wherein the maintaining step further comprises heating the blank by an electrical heating process selected from the group consisting of radiant, joulian and induction heating.

36. The method of claim 34 wherein the maintaining step further comprises heating the blank in a bath of heated liquid.

37. The method of claim 36 wherein the bath is comprised of a salt solution.

38. The method of claim 26 wherein the grinding step is performed using a rotary grinding wheel having a surface speed of between about 3,000 and 8,000 surface feet per minute.

39. The method of claim 38 wherein the surface of the grinding wheel is flat.

40. The method of claim 38 wherein the surface of the grinding wheel is convex.

41. The method of claim 26 wherein the grinding step includes the steps of:

supporting at least one of said blanks;

fixing the blank at a predetermined position in relation to the grinding wheel;

grinding a first elongated narrow surface along the working length of the blank; and indexing the blank about its longitudinal axis and subsequently grinding another elongated narrow surface along the working length of the blank.

42. The method of claim 41 wherein the blank indexing and subsequent grinding steps are repeated at least twice after formation of the first elongated surface to form a preformed file blank having a substantially triangular cross section.

43. The method of claim 41 wherein the blank indexing and subsequent grinding steps are repeated at least three times after formation of the first elongated surface to form a preformed file blank having a substantially quadrilateral cross section.

44. The method of claim 41 wherein the blank is indexed approximately 90° during each indexing step.

45. The method of claim 41 wherein the blank indexing steps alternatively index the blank 60° and 120° to form a preformed file blank having a substantially rhomboidal cross section.

46. The method of claim 41 wherein the grinding step is performed using a rotary grinding wheel having a surface speed of between about 3,000 and 8,000 surface feet per minute.

47. The method of claim 46 wherein the grinding step is performed using a rotary grinding wheel having a surface speed of about 5,000 surface feet per minute.

48. The method of claim 41 wherein the grinding step is performed using a rotary grinding wheel having a surface speed of between about 3,000 and 8,000 surface feet per minute and a material feed rate of between about 50 and 100 lineal feet per minute.

49. The method of claim 41 wherein the grinding step is performed using a rotary grinding wheel having a surface speed of about 5,000 surface feet per minute and a material feed rate of between about 50 and 100 lineal feet per minute.

50. The method of claim 49 wherein the material feed rate is about 75 lineal feet per minute.

51. The method of claim 22 wherein the maintaining step further comprises the step of heating the blank to a temperature above the austenite finish temperature Af of the superelastic material during twisting.

52. The method of claim 51 wherein the heating step includes electrically heating the blank in a process selected from the group consisting of radiant, joulian and induction heating.

53. The method of claim 51 wherein the heating step includes submerging the blank in a bath of heated liquid.

54. The method of claim 53 wherein the bath is comprised of a salt solution.

55. The method of claim 53 wherein the bath is comprised of oil.

56. The method of claim 51 wherein the heating step is caused by internal friction of twisting, without the application of heat from an external heat source.

57. A method of making a file from a rod formed of a superelastic material and having a first and a second end and a working length therebetween, the method comprising the steps of:

grinding the rod to form a file preform having a predetermined length, cross-sectional shape and taper along the working length thereof, the cross-sectional shape having corners which define longitudinal edges along the working length; and twisting the preform to permanently helically deform said preform and form helical shaped cutting edges from said longitudinal edges.

58. The method of claim 57 wherein the preform is maintained in an austenite phase until immediately prior to twisting.

59. The method of claim 57 wherein the preform is transformed to the martensite phase during twisting.

60. The method of claim 57 further comprising the step of heating the preform to a temperature above the austenite finish temperature Af of the material prior to twisting.

61. The method of claim 57 wherein the grinding step includes the steps of:

retaining at least one rod in a predetermined position with respect to a grinding wheel;

grinding a first elongate narrow surface along the working length of the rod; and alternatively indexing the rod about a longitudinal axis thereof and subsequently grinding another elongate narrow surface along the working length of the rod.

62. The method of claim 61 wherein the preform is maintained in the austenite phase of said material until immediately prior to twisting.

63. The method of claim 61 wherein the preform is transformed to the martensite phase of said material by twisting.

64. The method of claim 61 further comprising the step of heating the preform to a temperature above the austenite finish temperature Af of the material prior to twisting.

65. The method of claim 64 wherein the grinding step is performed using a rotary grinding wheel having a surface speed of about 5,000 surface feet per minute.

66. The method of claim 61 wherein the grinding step is performed using a rotary grinding wheel having a surface speed of between about 3,000 and 8,000 surface feet per minute.

67. The method of claim 61 wherein the grinding step is performed using a rotary grinding wheel having a surface speed of between about 3,000 and 8,000 surface feet per minute and a material feed rate of between about 50 and 100 lineal feet per minute.

68. The method of claim 67 wherein the material feed rate is about 75 lineal feet per minute.

69. The method of claim 61 wherein the grinding step is performed using a rotary grinding wheel having a surface speed of about 5,000 surface feet per minute and a material feed rate of between about 50 and 100 lineal feet per minute.

70. The method of claim 61 wherein the grinding step is performed with a rotatable grinding wheel having a surface which is convex.

71. The method of claim 61 wherein the grinding step is performed with a grinding wheel having surface which is concave.

72. The method of claim 61 wherein the rod is indexed and ground two times after formation of the first elongate narrow surface to form a preform having a substantially triangular cross section along the working length.

73. The method of claim 72 wherein the rod is alternatively indexed approximately 60° and approximately 120° to form a file having a substantially rhomboidal cross section.

74. The method of claim 61 wherein the rod is indexed and ground three times after formation of the first elongate narrow surface to form a preform having a substantially quadrilateral cross section along the working length.

75. The method of claim 61 wherein the rod is indexed approximately 90° after formation of each elongate narrow surface.

76. The method of claim 57 wherein the grinding step is performed upon a single rod retained in a rotatable collar.

77. The method of claim 57 wherein the grinding step is performed upon a plurality of rods disposed in side-by-side parallel relationship.

78. The method of claim 57 wherein a plurality of rods are retained, in side-by-side parallel relationship, upon a rest by a movable retainer.

79. The method of claim 57 further comprising the step of: heating the preform by an electrical heating process selected from the group consisting of radiant, joulian and induction heating.

80. The method of claim 57 further comprising the step of: heating the preform by internal friction during the twisting step.

81. The method of claim 80 wherein the liquid is comprised of a salt solution.

82. The method of claim 80 wherein the liquid is comprised of oil.

83. The method of claim 82 wherein, the rotating step is performed at a predetermined rotation rate;

the distance increasing step is performed at a predetermined axial speed; and further comprising the step of:

controlling the rotation rate and the speed to form a file having a predetermined twist rate.

84. The method of claim 57 further comprising the step of: heating the preform in a bath of heated liquid.

85. The method of claim 57 wherein the twisting step includes the steps of:

securing the first end of the file preform in a rotatable collet;

securing the working length of the preform at a position proximate to the collet in a slidable non-rotatable work holder at a predetermined distance from said collet;

rotating the collet and the portion of the file preform proximate the collet; and increasing the distance between said collet and said work holder.

86. A superelastic endodontic file comprising:

a shaft formed from a superelastic rod having a working length;

at least three cutting apices with adjacent cutting apices defining surfaces therebetween, said apices being permanently helically deformed along the working length of said shaft to form helically shaped cutting edges;

wherein the surfaces of the shaft between adjacent longitudinal cutting edges define elongated helical surfaces which are flat when viewed in transverse cross section.

87. A superelastic endodontic file comprising:

a shaft formed from a superelastic rod having proximal and distal ends with a working length therebetween, said proximal end including a handle section and said distal end including a tip;

four or more cutting apices helically arranged about said shaft along the working length;

wherein the working length of said shaft includes a transverse cross-sectional area which is substantially rhomboidal in shape.

88. The endodontic file of claim 87 wherein the working length is tapered such that the rhomboidal shape decreases in area toward the tip.

89. An endodontic file having a predetermined transverse cross-sectional shape including corners, the file comprising:

integral working length and handle sections formed of a material exhibiting superelasticity above an austenitic finish temperature Af of the material with said working length having the predetermined transverse cross-sectional shape, said working length being twisted about its longitudinal axis to permanently form helical cutting edges at the corners thereof.

90. The endodontic file of claim 89 wherein said material is selected from the group consisting of near-equiatomic Ni-Ti, Ni-Ti-Nb alloys, Ni-Ti-Fe alloys, Ni-Ti-Cu alloys, Ni-Ti-Nb alloys, beta-phase titanium and combinations thereof.

91. The endodontic file of claim 89 wherein said material is at least about 40 atomic percent Ti.

92. The endodontic file of claim 89 wherein said material is about 50.8 atomic percent Ti and about 49.2 atomic percent Ni.

93. The endodontic file of claim 89 wherein said predetermined transverse cross-sectional shape is selected from the group consisting of three and four sided polygons.

94. The endodontic file of claim 89 wherein said predetermined transverse cross-sectional shape is substantially rhomboidal.

95. The endodontic file of claim 94 wherein said rhomboidal shape has angles of about 60°–120°–60°–120°.

96. An endodontic file comprising:

a shaft including a working length portion formed of a material exhibiting superelastic characteristics, said working length portion having a predetermined transverse cross sectional area, a longitudinal axis, and a plurality of apices defining cutting edges, said working length portion being permanently plastically deformed by twisting about its longitudinal axis to form said cutting edges at the apices thereof.

97. The endodontic file of claim 96 wherein said working length includes at least three of said cutting edges helically arranged about the working length of said shaft.

98. The endodontic file of claim 96 further comprising:

helical surfaces arranged between adjacent cutting edges, said helical surfaces being substantially flat when viewed in transverse cross section.

99. The endodontic file of claim 96 wherein said working length includes at least four of said cutting edges helically arranged along said shaft.

100. The endodontic file of claim 99 further comprising: a flat side arranged between adjacent cutting edges.

101. The endodontic file of claim 96 wherein said metal is selected from the group consisting of near-equiatomic Ni-Ti, Ni-Ti-Nb alloys, Ni-Ti-Fe alloys, Ni-Ti-Cu alloys, Ni-Ti-Nb alloys and beta-phase titanium.

102. The endodontic file of claim 96 wherein said metal is at least about 40 atomic percent Ti.

103. The endodontic file of claim 96 wherein said material is about 50.8 atomic percent Ti and about 49.2 atomic percent Ni.

104. The endodontic file of claim 96 wherein said predetermined transverse cross-sectional shape is selected from the group consisting of three and four sided polygons.

105. The endodontic file of claim 96 wherein said predetermined transverse cross-sectional area has a substantially rhomboidal shape.

106. The superelastic file of claim 105 wherein said substantially rhomboidal shape has angles of about 60°–120°–60°–120°.

107. Apparatus for forming an endodontic instrument from a superelastic rod-shaped blank, the apparatus comprising:

a linear motion mechanism including a clamping element for holding a portion of said blank and moving said clamping element along said blank;

a rotary motion mechanism for holding and rotating said instrument, said rotary motion mechanism being operatively coupled to said linear motion mechanism for rotating said blank as said clamping element moves therealong to form a helically fluted instrument; and a source of heat disposed proximate said linear and rotary motion mechanisms for heating said blank at least prior to operation of the linear and rotary motion mechanisms.

108. The apparatus of claim 107 wherein the source of heat is an electrical heating source selected from the group consisting of radiant, joulian and conductive types of heating sources.

109. The apparatus of claim 107 wherein the source of heat is a heated liquid.

110. The apparatus of claim 109 wherein said liquid is contained in a vessel operatively coupled to a heating element with said linear and rotary motion mechanisms mounted above said vessel for vertical movement into said vessel.

111. The apparatus of claim 110 wherein said liquid contains a salt.

112. The apparatus of claim 107 wherein said rotary motion mechanism includes a collet adapted to hold an endodontic file blank.

* * * * *

UNITED STATES PATENT AND TRADEMARK OFFICE
CERTIFICATE OF CORRECTION

PATENT NO. : 6,149,501
DATED : November 21, 2000
INVENTOR(S) : Farzin-Nia et al.

Page 1 of 1

It is certified that error appears in the above-identified patent and that said Letters Patent is hereby corrected as shown below:

<u>Column 6,</u>
Line 30, reads "C-601V" and should read -- 601V --.

Table 2, size 60, column L reads "22.35-20.95" and should read -- 22.35-20.98 --.

Signed and Sealed this

Thirtieth Day of October, 2001

Attest:

*Nicholas P. Godici*

NICHOLAS P. GODICI
*Attesting Officer*     *Acting Director of the United States Patent and Trademark Office*